US011191454B2

(12) United States Patent
Sashen

(10) Patent No.: US 11,191,454 B2
(45) Date of Patent: Dec. 7, 2021

(54) BIOFEEDBACK FOR ALTERING GAIT

(71) Applicant: FEEL THE WORLD, INC., Broomfield, CO (US)

(72) Inventor: Steven Sashen, Superior, CO (US)

(73) Assignee: FEEL THE WORLD, INC., Broomfield, CO (US)

( * ) Notice: Subject to any disclaimer, the term of this patent is extended or adjusted under 35 U.S.C. 154(b) by 0 days.

(21) Appl. No.: 17/269,398

(22) PCT Filed: Aug. 29, 2019

(86) PCT No.: PCT/US2019/048682
§ 371 (c)(1),
(2) Date: Feb. 18, 2021

(87) PCT Pub. No.: WO2020/047179
PCT Pub. Date: Mar. 5, 2020

(65) Prior Publication Data
US 2021/0244318 A1    Aug. 12, 2021

Related U.S. Application Data

(60) Provisional application No. 62/725,900, filed on Aug. 31, 2018.

(51) Int. Cl.
*A61B 5/11* (2006.01)
*A61B 5/00* (2006.01)

(52) U.S. Cl.
CPC ............ *A61B 5/112* (2013.01); *A61B 5/1118* (2013.01); *A61B 5/1123* (2013.01); *A61B 5/486* (2013.01)

(58) Field of Classification Search
CPC ..... A61B 5/112; A61B 5/1118; A61B 5/1123; A61B 5/486
(Continued)

(56) References Cited

U.S. PATENT DOCUMENTS 5,449,002 A    9/1995    Goldman
7,618,347 B2   11/2009   Yeo et al.
(Continued)

FOREIGN PATENT DOCUMENTS

CN    106267780 A    1/2017
CN    107944431 A    4/2018
(Continued)

OTHER PUBLICATIONS

International Search Report and Written Opinion issued in International Patent Application No. PCT/US2019/048682 dated Jan. 2, 2020 (11 pages).
(Continued)

*Primary Examiner* — Robert P Bullington
(74) *Attorney, Agent, or Firm* — Dorsey & Whitney LLP

(57) ABSTRACT

The present disclosure relates generally to a method for providing motion biofeedback to a user while the user performs an activity, where the biofeedback can occur in real time or after discrete points in time (e.g., after a drive phase or maximum velocity phase). The method includes determining an activity type performed by the user; determining a target value for one or more motion characteristics associated with the activity, wherein the target value is determined by historical collected motion data; receiving motion data related to the activity as the user performs the activity; comparing the motion data to the target value; and transmitting feedback to a feedback device based on the comparison to the target value, wherein the feedback corresponds to a motion adjustment proportional to a deviation of the motion data relative to the target value.

11 Claims, 4 Drawing Sheets

(58) Field of Classification Search
USPC .......................................................... 600/595
See application file for complete search history.

(56) References Cited

U.S. PATENT DOCUMENTS

| | | | |
|---|---|---|---|
| 7,771,371 B2 | 8/2010 | Avni | |
| 7,927,253 B2 | 4/2011 | Vincent et al. | |
| 8,979,665 B1* | 3/2015 | Najafi | A63B 69/3608 |
| | | | 473/269 |
| 9,625,485 B2 | 4/2017 | Oleson et al. | |
| 9,642,415 B2 | 5/2017 | Pease et al. | |
| 10,062,297 B2 | 8/2018 | Dibenedetto et al. | |
| 11,128,636 B1* | 9/2021 | Jorasch | G06F 3/017 |
| 2011/0152696 A1 | 6/2011 | Ryan | |
| 2014/0156215 A1* | 6/2014 | Eastman | A61B 5/112 |
| | | | 702/141 |
| 2016/0166178 A1 | 6/2016 | Fuss et al. | |
| 2016/0284231 A1* | 9/2016 | Walsh | A61B 5/6828 |
| 2018/0177436 A1 | 6/2018 | Chang et al. | |

FOREIGN PATENT DOCUMENTS

| | | | |
|---|---|---|---|
| CN | 108073287 A | 5/2018 | |
| DE | 102018100201 A1 | 7/2018 | |
| WO | 2019/086997 A2 | 5/2019 | |

OTHER PUBLICATIONS

International Search Report and Written Opinion dated Jan. 2, 2020, in PCT Application No. PCT/US2019/048682, 11 pages.
Office Action issued in Chinese Patent Application No. 201980064699.9 dated Sep. 27, 2021 (7 pages).
Extended European Search Report issued in European Patent Application No. 19853345.7 dated Oct. 14, 2021 (10 pages).

* cited by examiner

BIOFEEDBACK FOR ALTERING GAIT

CROSS REFERENCE TO RELATED APPLICATIONS

This application is a national stage application under 35 U.S.C. § 371 of International Application No. PCT/US2019/048682 filed 29 Aug. 2019, entitled "Biofeedback for Altering Gait", which claims the benefit of U.S. Provisional Application No. 62/725,900, filed 31 Aug. 2018, and entitled "Biofeedback for altering gait," the entirety of each of which is incorporated herein by reference for all purposes.

TECHNICAL FIELD

The technology described herein relates generally to systems and methods for detecting and providing feedback to a user regarding a user's gait or other motion.

BACKGROUND

Running and walking are activities performed by people daily. However, many people are unaware of how their motion, force application, etc. during these activities may be inefficient, potentially damaging to their bodies, or the like. Conventional techniques for improving running or walking form include a coach visually watching a person during the activity and providing instruction. However, this limits the person's ability for instruction to the monitored activity times, is time intensive, and is limited to the particular coach or instructor's expertise.

The information included in this Background section of the specification, including any references cited herein and any description or discussion thereof, is included for technical reference purposes only and is not to be regarded subject matter by which the scope of the invention as defined in the claims is to be bound.

SUMMARY

In some embodiments, a method for providing motion feedback to a user is disclosed. The method includes determining, by a processor, an activity type performed by the user; determining, by the processor, a target value for one or more motion characteristics associated with the activity, where the target value is determined by historical collected motion data; receiving, from a detection device, motion data related to the activity as the user performs the activity; comparing, by the processor, the motion data to the target value; and transmitting feedback to a feedback device based on the comparison to the target value, wherein the feedback corresponds to a motion adjustment proportional to a deviation of the motion data relative to the target value. The motion detected may include ground contact time, impact forces, impact force vectors, and other detectable characteristics of a person during an activity, such as walking, running, sprinting, and so on.

In some embodiments, a method of providing feedback to a user for a plurality of motion activity, such as sprinting, running and walking, is disclosed. The method includes receiving, from a first detection device, a first motion characteristic value corresponding to a first motion characteristic, the first motion characteristic having a first stored target value; receiving, from a second detection device, a second motion characteristic value corresponding to a second motion characteristic, the second motion characteristic having a second stored target value; comparing, by a processor, the first motion characteristic value to the first stored target value to determine a first deviation amount corresponding to a deviation of the first motion characteristic value relative to the first stored target value; comparing, by a processor, the second motion characteristic value to the second stored target value to determine a second deviation amount corresponding to a deviation of the second motion characteristic value relative to the second stored target value; and transmitting, by the processor, a first feedback related to the first deviation amount and a second feedback related to the second deviation amount, wherein the first feedback corresponds to a first motion adjustment related to the first motion characteristic, the first motion adjustment in proportion to the first deviation amount, the second feedback corresponds to a second motion adjustment related to the second motion characteristic, the second motion adjustment in proportion to the second deviation amount, and the first feedback is different than the second feedback.

In some embodiments, a method of providing motion feedback to a sprinter is disclosed. The method includes receiving, from a detection device, first motion data corresponding to ground contact force and second motion data corresponding to force vector angle of the ground contact; comparing, by a processor, the first motion data to an ideal ground contact force value, wherein the ideal ground contact force value is an indicator of improved sprinting performance; comparing, by the processor, the second motion data to an ideal force vector angle value, wherein the ideal force vector angle value is an indicator of improved sprinter form; generating, by the processor, first feedback to be provided to a user via a feedback device corresponding to an adjustment in ground contact force based on the comparison of the first motion data to the ideal ground contact force value, and second feedback corresponding to an adjustment in force vector angle based on the comparison of the second motion data to the ideal force vector angle value.

In some embodiments, a method for providing stage-specific motion feedback to a user is disclosed. The method includes determining, by a processor, an activity type performed by the user; receiving, from a detection device, motion data comprising a motion characteristic value corresponding to a motion characteristic associated with the activity type; determining, by the processor, a current activity stage based on the activity type and detected motion data; determining, by the processor, an ideal value for the motion characteristic based on the current activity stage; comparing, by the processor, the motion characteristic value to the ideal value to determine a motion adjustment to achieve the ideal value; and generating, by the processor, feedback related to the motion adjustment, wherein the feedback is dependent on the activity stage.

This Summary is provided to introduce a selection of concepts in a simplified form that are further described below in the Specification. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments and implementations and illustrated in the accompanying drawings.

DETAILED DESCRIPTION

In some embodiments herein a system and device for detecting, analyzing, and providing feedback to a user related to his or her motion, such as running or walking, is disclosed. The system may include one or more devices, e.g., wearable sensors, attached to a user or a user's accessories, such as a user's shoe, clothing, leg, arm, or the like, that detect various motion-related characteristics (e.g., user applied forces and movement information) during the motion activity. Illustrative motion-related characteristics include cadence, stride length, vertical loading forces at and during ground contact, deceleration/acceleration at and during ground contact, angle of a force vector at and during ground contact, duration of ground contact, and/or vertical displacement throughout the movement or gait cycle.

The detected characteristics are then analyzed by one or more processing elements to output a feedback value. The feedback value may be compared relative to predetermined ideal range or threshold to determine if a user needs to vary the motion in any manner, such as to result in a more efficient or improved motion range or the like. The system provides biofeedback to the user in real time, such as through audible, visual, and/or tactile sensations indicating the difference between the feedback value generated by their current movement pattern in relation to more ideal feedback values. For example, select tones may be transmitted to the user via headphones or a speaker, where the pitch, volume, or the like, varies in relation to the feedback value and/or the recommended change. As another example, an electrical pulse or vibration can be delivered to the user's skin (e.g., through a wearable watch, bracelet, fitness tracker, etc.), where the strength, repetition, location, or the like, of the sensation corresponds to the recommended change or the feedback value. As yet another example, visual indicators can be presented through a display (e.g., television, glasses, virtual reality headset, or other electronic display), that correlate to the recommended change.

The real time detection, analysis, and feedback to the user, during the motion activity, allows the user to adjust, in real time, his or her motion, to improve gait, performance, or the like. The detected characteristics and feedback values can be changed dynamically based on the user's skill level, desired goals (e.g., faster run times, longer strides), injuries, or the like. Further, because the feedback is based on predetermined ranges or thresholds, the user will receive consistent instruction for motion changes.

Figure 1A:
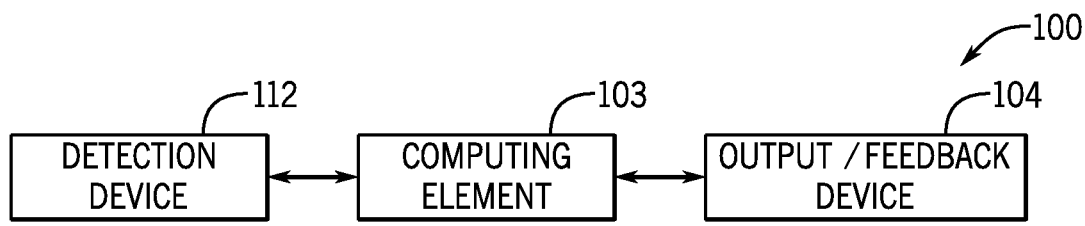
FIG. 1 is a schematic view of a system for providing biofeedback corresponding to physical motion by a user.

Turning to the figures, a system for providing motion feedback to a user will now be discussed. FIG. 1A shows a system for detecting and providing feedback to a user during motion. The system 100 may include a detection device 112, a computing element 103, and an output/feedback device 104. The detection device 112 may detect motion characteristics generated during an activity (e.g., walking, jogging, running, sprinting, aerobics, plyometrics, etc.). The detection device may be connected or coupled to a user such that it moves with or is able to detect movement by the user, e.g., the detector may be attached to a user's shoe, chest strap, belt, clip connected to clothing, headband, ear insert, or the like. The computing element 103 may include a processor capable of analyzing the detected motion characteristics to determine whether the motion characteristics are ideal or within a selected value or should be adjusted. The output/feedback device 104 provides visual, tactile/haptic, auditory, and/or olfactory feedback to a user. The feedback provided by the feedback device 104 corresponds to change of the user's motion to output values in relation to a recommended value or an ideal or target value, e.g., the feedback changes correspondingly as the user motion approaches/departs towards an ideal or target value. For example, the feedback may increase in intensity as the user falls father behind a desired motion output or may decrease in intensity as the user approaches the desired motion output. The corresponding nature of the feedback to the user's output assists the user in manipulating his or her activity and motion characteristics to home in on the desired target values.

Figure 1B:
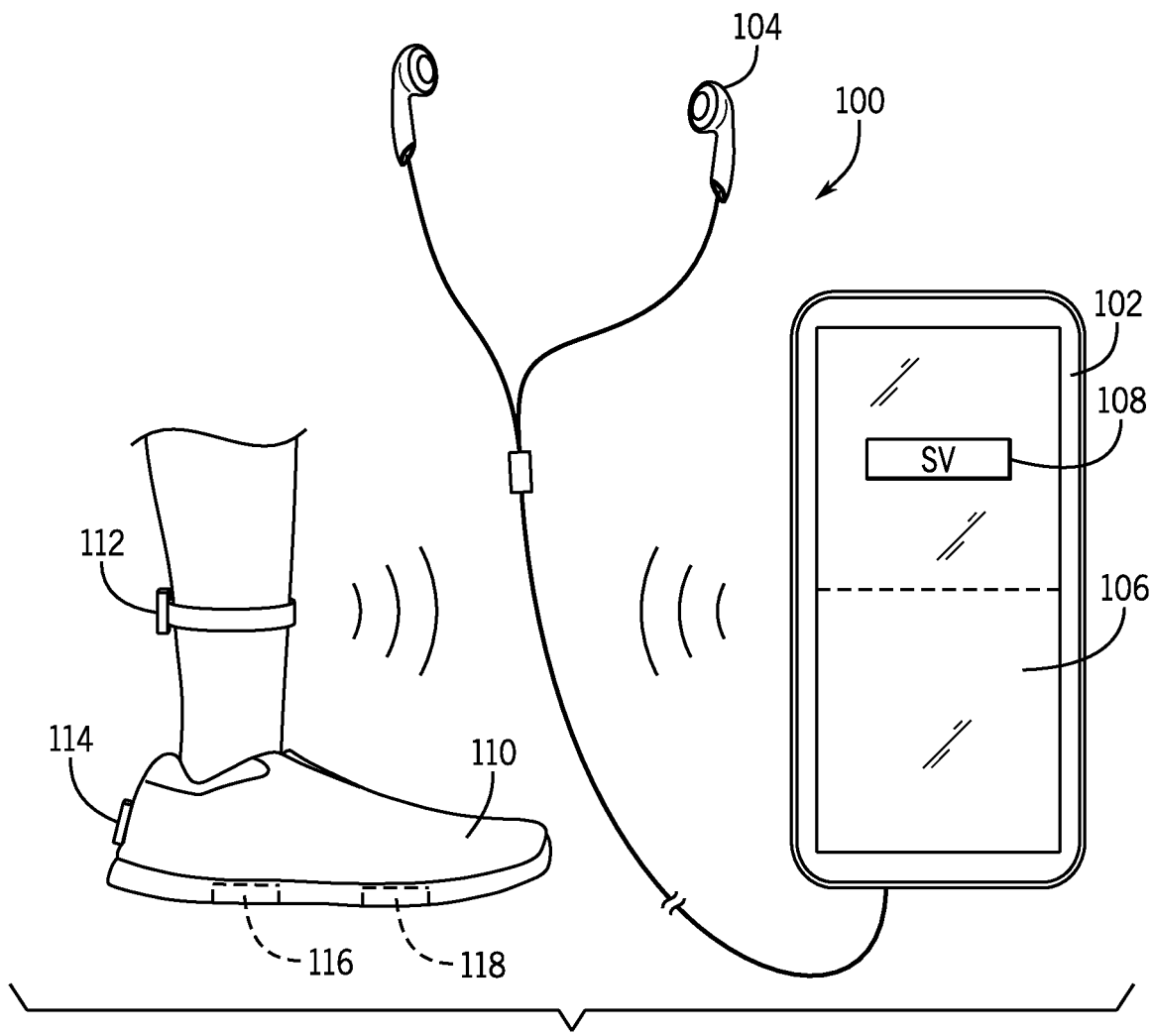

FIG. 1B shows an exemplary system for the system of FIG. 1A. The system 100 may include one or more user devices 102, such as mobile computing device (e.g., cell phone, mobile gaming device, etc.), feedback devices 104 (e.g., headphones, glasses, visual display 106, wearable device 112), or the like, and one or more detection devices (e.g., wearable device 112, 114; sensors 116, 118), each discussed below.

The various components of the system 100 may be in communication with one another such as through a network, radio transmissions (Bluetooth, WiFi, ZigBee, BLE, etc.), or hardwired connections. In this manner, data can be readily transmitted between the devices and then presented to the user as needed. Further, in some instances, the devices may transmit and/or receive data from a server, e.g., a cloud network, or the like.

As mentioned above, the user device 102 may be a mobile cellular phone, gaming device, wearable computing device (e.g., smartwatch, smart glasses), computer, or the like. Often, the user device 102 may be mobile and carried with the user during the motion in order to provide computing power to analyze the user's motion, but in some embodiments, the computing functionality may be incorporated into the feedback and/or detection devices and the user device 102 can be omitted. The user device 102 may include a display screen 106 that provides a graphical user interface 108 to the user including feedback icons and elements that illustrate the current motion analysis of the user.

The feedback devices 104 may be substantially any type of device for providing a visual, audible, or physical sensation (e.g., mechanical or electrical pulse) to a user. In one embodiment, the feedback device 104 may be headphones for providing audible information to a user. In another example, the feedback device 104 may be a visual device, such as smart glasses, bionic lenses, goggles, or the like, and include varying colors and lights to present information to a user. In another example, the feedback device 104 may be in contact (directly or indirectly) with a user's skin to provide a tactile or electrical sensation (e.g., pulse, wave, etc.) to provide information to the user. Often, the feedback device 104 may be configured to deliver two or more types of feedback to the user, e.g., audible and tactile sensations, which may be used simultaneously or separately to deliver different types of information.

The detection devices 112, 114 may include one or more sensors 116, 118 (either integrated therein or in communication therewith). The detection devices 112, 114 are configured to be worn or otherwise secured to the user such that movement by the user moves the detection devices 112, 114 correspondingly. In many instances, the system 100 may include a single detection device 112, 114 but in other embodiments may include two or more detection devices. The detection devices 112, 114 may be a wearable device, e.g., ankle strap, wrist strap, chest strap, belt, clip (e.g., for clipping onto plants), ear bud or headphone, headband, or other attachment to another part of the body, and/or may be incorporated or configured to attach to a user worn accessory, e.g., shoe(s), clothing, gloves, headware, or the like, and may be configured to detect biometric values of the user (e.g., heart rate). In some embodiments, the positioning and connection to the user depends on the desired motion to be tracked. For example, to detect walking or running movement characteristics, the detection device 112, 114 may be connected near or on the user's legs or feet (e.g., ankle strap), such that as the user moves his or her leg the detection device 112, 114 moves therewith. In other examples, the detection device 112, 114 may be embedded in a user's shoe 110, such as attached to the top and/or side of the shoe, an insert placed in a shoe, e.g., within an insole or footbed, or the like. In other embodiments, the detection device 112, 114 may be positioned and connected to the user in a different area than the motion to be tracked. For example, the detection device may be located near the user's head (e.g., one or more ear buds), but may be used to track motion near the user's legs (e.g., walking or running motion).

The sensors 116, 118 (which may be incorporated into the detection device 112, 114) include one or more accelerometers (e.g., a 9-axis sensor that may include a 3-axis accelerometer, 3-axis gyroscope, 3-axis magnetometer, and/or a compass), gyroscopes, pressure or force sensors, location sensors (global positioning system sensors), and the like. In some instances the detector device may include multiple sensors (e.g., a 9 axis accelerometer that includes three different three axis accelerometers, a 7 axis sensor with two three-axis devices and a single axis device, etc.) or the detection device may include a single sensor, such as one accelerometer. The configuration of the detection device may be varied depending on the motion characteristics detected. The sensors 116, 118 may also be incorporated in the user device 102, such that the detection device 112, 114 may include a first group of sensors, e.g., accelerometers and force sensors, and the user device 102 may include the GPS sensors and/or image detection sensors. The sensors 116, 118 may be positioned through the system 100 depending on the desired characteristics to be tracked.

Figure 2:
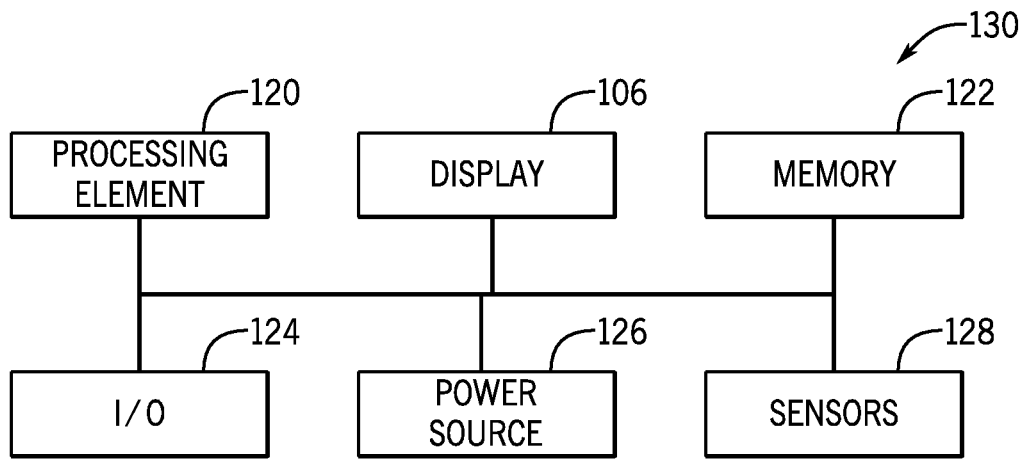
FIG. 2 is a simplified block diagram of select aspects of the system of FIG. 1.

FIG. 2 illustrates an exemplary block diagram of the system 100 computing resources and components 130 that may be included in the various system 100 devices and/or shared across the system 100 by the various devices. The system 100 may include one or more processing elements 120, displays 106, one or more memory components 122, an input/output interface 124, a network interface 126, and the one or more sensors 128, each of which may be in communication either directly or indirectly.

The processing element 120 is any type of electronic device capable of processing, receiving, and/or transmitting instructions. For example, the processing element 120 may be a microprocessor or microcontroller. Additionally, it should be noted that select components of the system 100 may be controlled by a first processor and other components may be controlled by a second processor, where the first and second processors may or may not be in communication with each other. As one example, the detection devices 112, 114 or feedback devices 104 may include one or more processing elements 120 or may utilize processing elements included in other components of the system 100. In some embodiments, it is contemplated that all computation may be executed by a detection device 112, 114 and/or by a feedback device 104 (e.g. ear buds).

The display 106 provides visual output to a user and optionally may receive user input (e.g., through a touch screen interface). The display 106 may be substantially any type of electronic display, including a liquid crystal display, organic liquid crystal display, and so on. The type and arrangement of the display depends on the desired visual information to be transmitted to the (e.g., can be incorporated into a wearable item such as glasses, or may be a television or large display, or a screen on a mobile device).

The memory 122 stores data used by the system 100 to store instructions for the processing element 120, as well as store positional and content data for the system 100. For example, the memory 122 may store data or content, such as feedback reference ranges, values, images, graphics, and the like. The memory 122 may be, for example, magneto-optical storage, read only memory, random access memory, erasable programmable memory, flash memory, or a combination of one or more types of memory components.

The I/O interface 124 provides communication to and from the various devices within the system 100 and components of the computing resources to one another. The I/O interface 124 can include one or more input buttons, a communication interface, such as WiFi, Ethernet, or the like, as well as other communication components, such as universal serial bus (USB) cables, or the like.

The power source 126 provides power to the various computing resources and/or devices. The system 100 may include one or more power sources and the types of power source may vary depending on the component receiving power. The power source 126 may include one or more batteries, wall outlet, cable cords (e.g., USB cord), or the like.

The sensors 128 may include the motion detection sensors 116, 118 as well as other sensors incorporated into the system 100, e.g., image sensors (cameras), light sensors, or the like. The sensors 128 are used to provide input to the computing resources that can be used to analyze the user motion and/or supplement the motion data collected by the sensors 116, 118.

Figure 3:
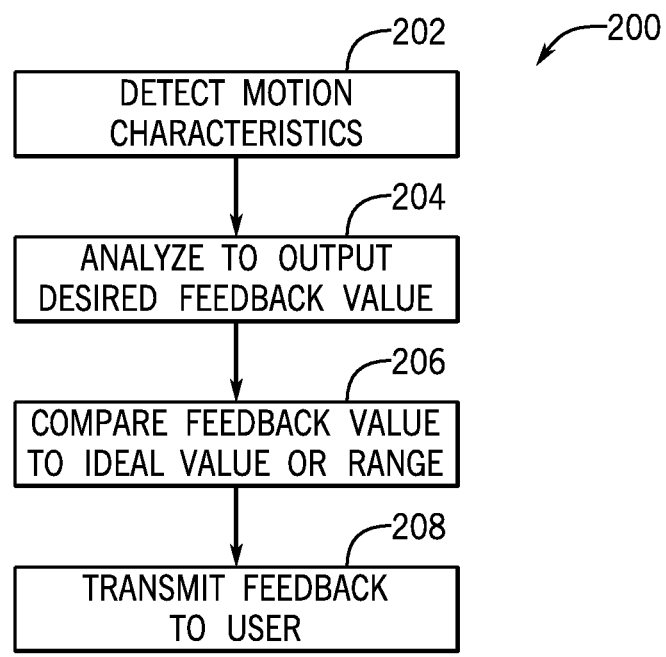
FIG. 3 is a flow chart illustrating a method for using the system of FIG. 1 to apply biofeedback to a user.

FIG. 3 illustrates a method for using the system 100 to analyze and provide motion feedback to a user related or corresponding to the user's motion (e.g., biofeedback). With reference to FIG. 3, the method 200 may begin with the sensors 116, 118 detecting one or more characteristics of the user's motion. For example, the user may begin to run or walk, moving his or her legs, moving the detection device 112, 114, correspondingly. As the user's legs move, his or her feet impact the ground alternatingly. As this occurs, the sensors 116, 118 detect variations in characteristics such as force, acceleration, angle, positioning, and the like. Examples of detected characteristics include vertical loading forces at and during ground contact, deceleration/acceleration forces at and during ground contract, one or more force vector angles at and during contact, ground contact duration, and/or vertical displacement through the gait or other movement cycle. The ground contact duration may be determined by the force experienced by the sensors 116, 118, light sensors (e.g., light levels change as the user's foot is on the ground covering/uncovering a sensor), tactile sensors, and so on. The sensors may be configured to detect characteristics over a select period of time and/or may detect only changes in a baseline, or the like.

As the motion characteristics are detected, the data is transmitted to the processing element 120 and the method 200 proceeds to operation 204. In operation 204, the processing element 120 analyzes the various detected characteristics to determine a feedback or analysis value. The feedback value may be a single value or may be multiple values, depending on the desired features of the system 100. The processing element 120 may combine one or more of the motion data depending on the system defaults and/or user selections, or detected motion (e.g., running vs. walking, sprinting versus distance running, running skill or level). In many embodiments, the feedback value is selected as a single "value" or number that can be easily understood by a user with respect to a range or threshold to understand the detected motion characteristics.

Examples of different feedback values include:
"Overstrider"—A scale measuring deceleration/acceleration on initial ground contact, where 0=no acceleration or deceleration; −100=complete deceleration (stopping); 100=doubling the rate of movement across the ground prior to ground contact.
"Overstride/Slammer"—A value calculated by multiplying the "Overstrider" value by vertical loading forces in Newtons upon ground contact.
"Reacher"—A scale of the angle of the force vector upon ground contact where 1=perpendicular to the ground; 100=1 degree above parallel to the ground in the opposite direction of movement.
"Reacher/Braker"—A value calculated by multiplying the "Reacher" value by the "Overstrider" value.
"Master"—A value calculated by multiplying any of the above values by the ground contact time In addition to the feedback values above, the processing element 120 may determine one or more derivative values of the recent history of originally calculated feedback values to return a derivative feedback value. Examples of derivative values including "Progress"—a moving average calculated by averaging the most recent set of values and/or "Improvement"—a weighted moving average determined by taking a select number of recent feedback value calculations, assigning a weight to each, where the more recent values have a higher weight and the sum of the total weights=100, multiplying the feedback values by their weights and averaging the weighted feedback values.

Once the processing element 120 has generated the one or more feedback values, the method 200 may proceed to operation 206. In operation 206, the processing element 120 compares the feedback values to one or more ranges or thresholds. The ranges or thresholds are selected based on approved or desired motion and force for the user. For example, exemplary stride lengths, ground force, contact time, and the like, are used to generate ideal values for each characteristic or feedback value. These ideal values are stored in the memory 122 and the processing element 120 compares the ideal values to the detected feedback values to determine whether the user's motion is falling above or below a desired goal. The ideal values vary based on the goals of the user, the motion or activity, the skill level of the user, the user's anatomy, and the like. The ideal values can be predetermined or generated based on an improvement plan for the user, e.g., dynamically update as the user progresses.

In some embodiments, ideal or target values may be preset incremental or percentage value relationships, such as, a value change over historical or last collected motion data (e.g., a previous detected motion characteristic). For example, an ideal or target value may be a percentage increase or decrease over the last collected value (e.g., increase force 5% over the last detected average for each new activity, decrease ground contact force 10% since the last detected ground force value or average from last activity). In this example, the ideal value may be scalable or variable as the value approaches a maximum or minimum. For example, the ideal or target value may be to increase ground force by 5% each run, until the exerted force reaches a certain threshold amount, then the ideal value may be scaled to increase force 1% each run, understanding that there may be a maximum level of force that is achievable. By using a preset incremental value or otherwise selecting the ideal or target value as a variable percentage of a historical value rather than an algorithm or predicted value, the system can more quickly determine motion adjustments (i.e., complicated algorithmic assessments are not needed) and more quickly provide feedback to a user as compared to instances where additional factors and relationships are determined and calculated. Further, basing the ideal or target values as a percentage relationship to previously detected values may reduce the data required to be stored and analyzed in real time.

After operation 206, the method proceeds to operation 208 and feedback is provided to the user, e.g., by the processing element transmitting data to the feedback devices 104 which provide the feedback to the user. For example, if the feedback value is at the correct, goal, or ideal range (e.g. as a percentage of the ideal value), the system may provide output positive feedback to the user, such as through the feedback devices 104. The positive feedback may include pleasurable tones, tactile sensations, audible encouragement, visually pleasing displays, or the like.

If in operation 206, the feedback values are below or above a selected range or threshold, the feedback is selected to correspond to the relative position of the feedback value relative to the ideal range or threshold, e.g., a low feedback value may result in a lower audible tone as compared to a high feedback value. As some examples, a tone or audio signal is provided to the user where the pitch or volume changes in relation to the value of the feedback value, such that a higher feedback value results in a higher pitch. As another example, the tone or audio signal may become more pleasing to the ears (e.g., softer, smoother, quieter, etc.) (i.e., "better" or more pleasant to the user) or less pleasing to the ears (e.g., harsher, more frequent, louder, etc.) (i.e., "worse" or less pleasant to the user) in relation to the amount of deviation of the calculated or detected value from the target value/range. As one example, a motion-related characteristic may have values that fit a bell-curve with the target value at the 50% mark. In this example, any deviation in either direction from the target value may be indicated by a "worse" tone. As another example, where there is a target range of values or a set target value, a detected value falling within the range of values or that matches the set value may be indicated by a positive tone (e.g., a tone that is pleasant to the ears, such as soft, quiet, and the like). In this example, the more the detected value deviates from the range or the set value, the "worse" the tone may become. As another example, an electrical pulse is delivered to the user's skin where the different feedback values result in different intensity, location, wave pattern, or the like of the pulse. As yet another example, a visual indicator is displayed on the display 106, such as colored lights, falling images, that may be presented within the user's line of sight and that correlate with the feedback value, e.g., a higher feedback value may result in an icon rising across the screen.

It should be noted that the various biofeedback provided to the user may be selected by the user (e.g., settings in an application executing on the user device 102), or may be preselected as defaults, or the like. The feedback is meant to be delivered to the user substantially simultaneously or as close to the actual movement generating the feedback values such that the user can correct or vary his or her motion in real time and be provided dynamically variable feedback adjusting to the user's changes. This allows a user to more easily adjust and correct their motion, as compared to conventional feedback mechanisms that are often separated from the motion in time (e.g., video tape analysis), and/or are inaccurate or variable (e.g., coach's verbal instruction).

Further, feedback may be different or distinguishable for different motion characteristics detected. For example, feedback may be provided related to both the ground contact force and force vector angle simultaneously or substantially simultaneously as both occur when contact with the ground is made. Feedback may differ for the different motion characteristics by type (e.g., visual, audible, haptic, etc.), presentation (e.g., type of visual presentation, volume, pitch, type of sound, etc.), location (e.g., vibration on the top or bottom of the wrist), frequency (e.g., many quick vibrations vs. slow, long vibrations), and the like. By providing different types of feedback for different motion characteristics, a user can assess how to adjust the user's motions to correct separate characteristics. In this manner, a user can make adjustments to improve performance while maintaining proper form. For example, certain systems may provide an integrated feedback that is generic to multiple detected characteristics or may provide feedback as to a single detected characteristic. In these instances, users may adopt their form to improve a single characteristic, at the detriment of their form, so while the feedback will seemingly improve, the user's actual form and other characteristics are degraded. As such, by providing distinguishable feedback for different characteristics, a user will look to adopt his or her motion to improve on all detected characteristics, resulting in an overall improvement in performance without sacrificing or degradation of his or her form. As a specific example, a first feedback is provided related to ground angle (e.g., over striding) and a second feedback is provided related to force, such that the user will want to improve both stride and force together, rather than adopting a stride that, while having a high force impact, will impact the overall performance of the user.

Figure 4A:
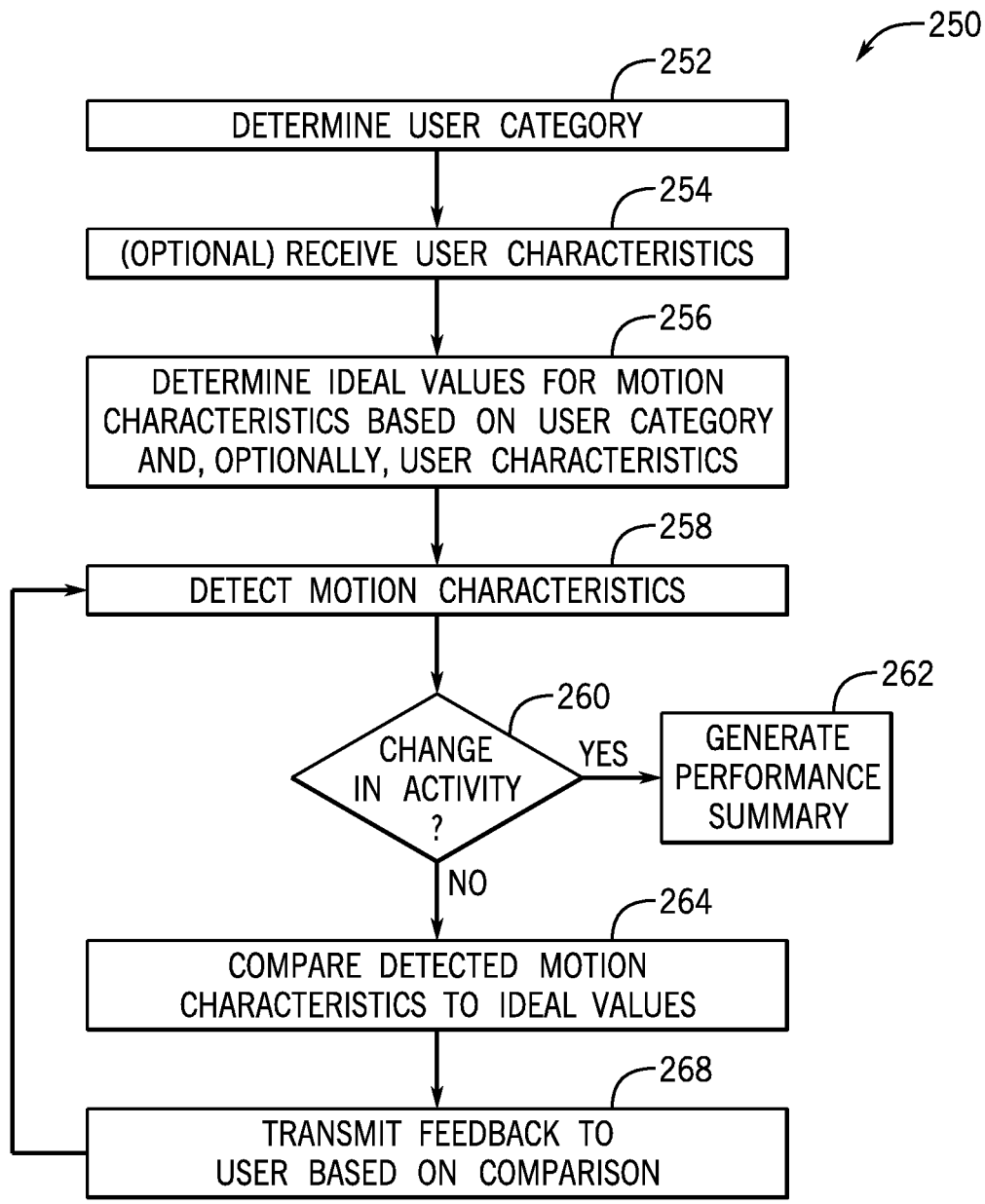
FIG. 4A is a flow chart illustrating a method for using the system of FIG. 1 to consistently track user movement and provide motion feedback to a user during a specific activity.

FIG. 4A illustrates a method for using the system 100 to consistently track user movement and provide motion feedback to a user during a specific activity. The method 250 begins with operation 252 and a user category is determined. A user category may define a type of activity having particular motion characteristics, as well as assist the system in determining the desired goal values for the user during the activity. For example, a user category may include a sprinter, long distance runner, jogger, walker, hiker, activity type (e.g., soccer, football, lacrosse, tennis, etc.) player, and the like. As one example, sprinters may generate characteristics tracking quick, forceful movements, while a long distance runner, jogger, or walker may generate characteristics with slower, less impactful movements.

The user category may be input by a user and/or determined by the system. For example, a user may select a user category before initiating the activity, e.g., a user may select on a user device the category applicable to the activity to be executed. For example, if a user is about to go for a long run, the user may select a long distance runner category. As another example, if the user is about to go for a walk, the user may select the walker category.

Figure 4B:
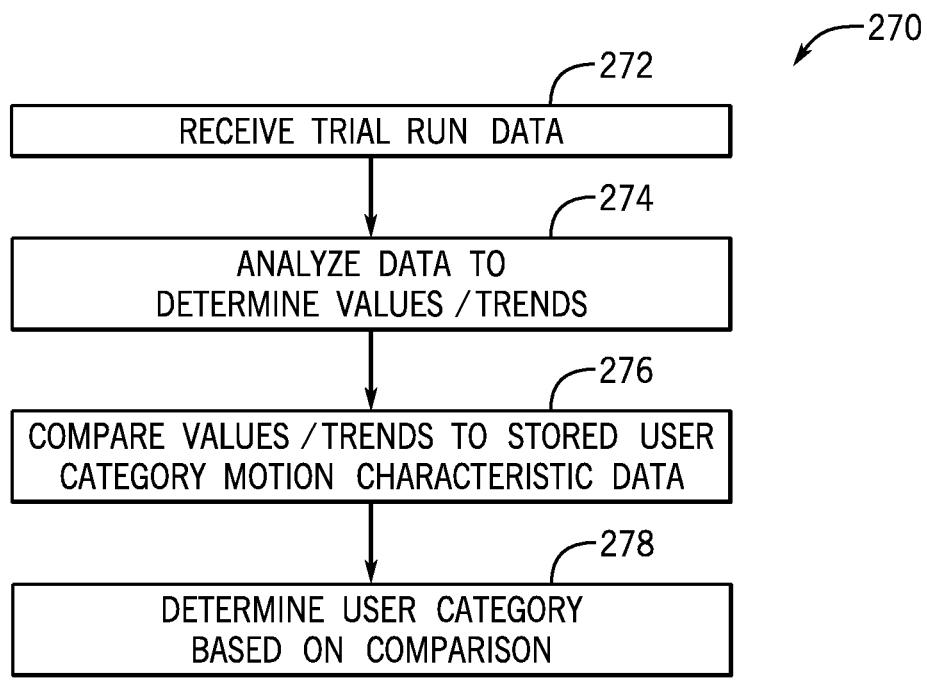
FIG. 4B is a flow chart illustrating a method for using the system of FIG. 1 to determine a user category based on collected motion data.

As another example, the system may determine the applicable user category based on detected user motions. For example, FIG. 4B illustrates a method for using the system 100 to determine a user category based on collected motion data. The method begins with operation 272 and trial run data is received. For example, a user may conduct an initial trial run as part of a registration process with the system or a trial may be instituted within the first few instances of a user's motion (e.g., 1-3 seconds or longer). An initial trial or sample run may be limited to a particular distance, number of strides, or time. For example, an initial trial run may include a minimum of 10 strides. The sensors track the motion characteristics during the trial run, such as data related to the user's range of motion, body positioning, forces (e.g., vertical ground contact force), speed, and the like.

After operation 272, the method 270 proceeds to operation 274 and the trial run data is analyzed to determine values and/or trends in the motion data. For example, the motion data may be analyzed to determine pace (e.g., distance over time), cadence (e.g., number of strides over time), ground contact time, vertical ground contact force, acceleration/deceleration at different times, and the like.

After operation 274, the method 270 proceeds to operation 276 and the system compares one or more of the determined values and/or trends to stored motion characteristic data related to user categories to determine the user category for the user. For example, a sprinter category may be associated with data indicative of a fast cadence (e.g., 190-280 strides per minute), short ground contact time (e.g., less than 160 milliseconds), greater vertical ground contact force, greater acceleration at the starting time, and the like, while a long distance runner category may be associated with data indicative of a slower cadence (e.g., 75-180 strides per minute), longer ground contact time (e.g., greater than 160 milliseconds), reduced vertical ground contact force, and the like. The system may use one or more determined values and/or trends, or any combination thereof, to determine the user category. For example, the system may use a combination of vertical ground contact force and ground contact time to determine the user category (e.g., a walker, jogger, long distance runner, sprinter, etc.).

After operation 276, the method 270 proceeds to operation 278, and the system determines the user category based on the comparison of determined values and/or trends to the stored data. For example, a determined value and/or trend may match a stored motion characteristic for a user category when the value and/or trend is the same as a motion characteristic value, fits within a range of values for a motion characteristic, or deviates from one or more values for the motion characteristic by a certain percent (e.g., 0.05% or less, 0.1% or less, 1% or less, 5% or less, etc.). The greater percentage of determined values/trends matching stored motion characteristics, the greater likelihood the motion data fits within the user category. For example, a user may have a determined cadence value of 185 strides per minute, which may be indicative of either a sprinter or a long distance runner. However, the system may determine the user fits within a sprinter category based on additional determined values/trends matching sprinter motion characteristics (e.g., short ground contact time, greater vertical ground contact force, greater acceleration at start, etc.), and not long distance runner motion characteristics. It should be noted that the category determination may be based on a single characteristic as well, such as arm speed, time of activity, force or the like, rather than multiple characteristics, in order to allow the system to more quickly estimate the type of activity in which the user is participating.

Returning to FIG. 4A, after the user category is determined at operation 252, the method 250 may proceed to operation 254 and user characteristics may be determined. For example, a user may input user characteristics into the system (e.g., via a graphical user interface) and/or the system may automatically detect characteristics, or may retrieve or access user characteristics from databases or other applications associated with the system 100. User characteristics may include, for example, gender, age, physique, height, weight, and other physical characteristics. Physique characteristics may include body type (e.g., slim, athletic, toned, overweight, etc.), limb/torso dimensions, foot size, and the like.

After operation 252, and optionally after operation 254, the method 250 proceeds to operation 256 and ideal values for motion characteristics are determined based on the user category and, optionally, the user characteristics. Ideal values may correspond to average values for professionals in the user category, average values for historical data collected by the system for the user category (e.g., collected from other users), average values for the particular user based on historical collected and stored data (e.g., from an initial trial run or previous recorded activities), percentage improvements over most recent collected data, values marked as ideal by a motion specialist (e.g., a coach, trainer, physical therapist, etc.), values marked as ideal by the user (e.g., targets or goals), and the like. For example, ideal values may indicate values for motion characteristics providing a strong overall performance during an activity, for example, by improving efficiency of energy use, reducing fatigue, reducing bodily impact (e.g., reducing injury), improving range of motion, improving posture, and the like.

As another example, where ideal values are based off average historical values for the particular user, the ideal values may be indicative of consistency for the user. As yet another example, where ideal or target values are based on percentage improvements over most recent collected data, the ideal values may be indicative of target incremental improvement goals. An ideal value may be a set value (e.g., an amount, percent, etc.), a threshold value (e.g., a minimum or maximum) or a range of values. An ideal value may be a qualitative or quantitative value. As one example, a qualitative ideal value may be a location of footstrike (e.g., mid-foot, ball of foot, etc.), a strike type (e.g., overstride, supinated, pronated, etc.), and the like. Ideal values may be stored by the system or by a third party database.

Ideal values may vary based on the user category. For example, ideal values for a long-distance runner may be different than ideal values for a sprinter. For example, a long distance runner may want to conserve energy for longer periods by reducing speed/cadence (e.g., 75-180 strides per minute), increasing ground contact time (e.g., 160-300 milliseconds or more), using less force per stride, and the like. A sprinter, on the other hand, may want to maximize energy during a short distance (e.g., to go as fast as possible) by increasing speed/cadence (e.g., 190-280 strides per minute), decreasing ground contact time (e.g., less than 200 milliseconds or less than 160 milliseconds), using more force per stride, and the like. As another example, an ideal footstrike for a runner may be the middle of the foot, while an ideal footstrike for a sprinter may be the ball of the foot (e.g., based on studies related to proper posture and reducing injury).

In some instances, ideal values may vary based on user characteristics. For example, ideal motions may vary based on physical characteristics, such as gender, age, physique, height, weight, and the like. As one example, an ideal cadence may vary based on user height. For example, an ideal cadence for a taller user (or an adult or a user with longer legs) may be slower than an ideal cadence for a shorter user (or a child or a user with shorter legs). An ideal value or range of values may vary across different categories or ranges of user characteristics. For example, an ideal value may be the same for women or men within a certain age range (e.g., 9-12 years old, 13-15 years old, 16-19 years old, 20-25 years old, 26-31 years old, 32-36 years old, etc.), height range (e.g., 5'0"-5'4", 5'5"-5'8", 5'9"-6'0", etc.), weight range (e.g., 110 lbs.-120 lbs., 121 lbs.-130 lbs., 131 lbs.-140 lbs., etc.), and the like, or any combination thereof. The system may determine which ideal values are applicable based on the received user characteristics. For example, an ideal value for a 5'2" woman weighing 125 lbs. may be determined based on an ideal value for women having a height between 5'0" and 5'4" and weight between 121 lbs.-130 lbs.

However, some ideal values may be consistent for a user category regardless of user characteristics. As one example, studies show that for ideal sprinting performance, ground contact should be with the ball of the foot. In this case, regardless of user characteristics, the ideal value for contact location is the ball of the foot. As another example, studies have shown that the ideal position for the foot to contact the ground is under or very near a person's center of mass to prevent overstriding. In this case, regardless of user characteristics, the ideal value for contact location is under or very near a person's center of mass.

In some instances, it may be desirable for a user to incrementally adjust his or her motions to consistently improve over time, e.g., towards a target end goal or without a target end goal. In these instances, the ideal value may be dependent on historical collected data, e.g., the last detected value or an average value for the last stored activity of the user. For example, the ideal value may be an amount of change (e.g., percent, angle, etc.) over the last detected value. For example, ideal values can be set as incremental values from the user's last detected characteristic towards a goal value, e.g., vary foot contact angle by 1 degree each stride, to assist a user in gradually reaching a desired value. As another example, incremental ideal values may be scalable as a maximum is reached. For example, it may be desirable for a runner to continuously increase ground contact force up to a maximum achievable force (e.g., based on the user's weight). For example, an ideal increase in contact force may be 5% each run. As the user approaches the maximum achievable force, the ideal incremental value may be scaled down, e.g., to 1% each run. As another example, it may be desirable for a runner to continuously reduce ground contact time to improve running efficiency. For example, a runner may decrease ground contact time by 10% each run. By providing preset incremental improvement targets (e.g., preset changes over prior collected data), the system reduces the factors needed to determine improvement. For example, a user may improve over the user's prior detected motion characteristic a certain amount regardless of the user's gender, age, physique, or the like.

After operation 256, the method 250 proceeds to operation 258 and motion characteristics are detected. A user may perform an activity, such as, for example, walking, jogging, running, sprinting, playing sports, aerobics, plyometrics, or the like. As discussed in more detail above, motion characteristics may be detected via one or more detection devices 112, 114 having one or more sensors 116, 118 (either integrated therein or in communication therewith). The detection devices 112, 114 are configured to be worn or otherwise secured to the user such that movement by the user moves the detection devices 112, 114 correspondingly. For example, the detection devices 112, 114 may detect motions correlated to gait, such as walking, jogging, running, or sprinting movement characteristics.

Certain motions may be monitored to determine speed, efficiency, proper posture, and other indicators of performance. For example, factors monitored (e.g., detected or determined by the system) that are related to movement performance (e.g., running, sprinting, etc.) may include ground contact time (e.g., amount of time feet are on the ground), ground contact balance (e.g., the difference between ground contact time on each foot), stride length, stride width (e.g., space between feet contacting ground), stride frequency (e.g., cadence), stride type (overstrider, reacher, collapser, weaver, bouncer, glute amnesiac, etc.), vertical force applied to ground (e.g., during a stride or a maximum amount), horizontal force, rate of force development, mass specific force (e.g., the amount of force applied in relation to bodyweight or mass), angle of force, momentum, resistance, acceleration/deceleration, center of mass/gravity (and vertical displacement thereof), support displacement (e.g., location of ground contact relative to center of mass), pace (e.g., distance over time), location of foot striking ground (e.g., footstrike based on acceleration/deceleration locations), and the like.

As one example, certain variables may be monitored based on the sprint velocity equation below:

$$V = f_{step} F_{avg} / W_b L_c$$

where V is the sprint velocity (m/s), $f_{step}$ is the step frequency (1/s), $F_{avg}$ is the average vertical force applied to the ground (N), $W_b$ is the body weight (N), and $L_c$ is the contact length (m) (e.g., the distance the person's center of mass translates over the course of one contact period). For example, an ideal sprint velocity for a sprinter is greater than an ideal sprint velocity for a long distance runner. Based on the above equation, a greater sprint velocity V correlates with greater step frequency $f_{step}$ and/or average vertical force applied to the ground $F_{avg}$, as well as lower body weight $W_b$ and/or contact length $L_c$. In one embodiment, the four variables may be detected by the system and input into the sprint velocity equation to determine the actual sprint velocity. The actual sprint velocity may be compared to an ideal sprint velocity value to determine adjustments to one or more of the input variables to achieve the ideal sprint velocity value. In another embodiment, if three of the four variables associated with sprint velocity V (e.g., $f_{step}$, $F_{avg}$, $W_b$, $L_c$) are detected by the system, an ideal value for the fourth variable may be determined based on an ideal value for the speed velocity V. For example, one or more sensors may detect or the system may determine the step frequency $f_{step}$, average vertical force applied to the ground $F_{avg}$, and the user's body weight $W_b$. The ideal value for sprint velocity V may be determined, e.g., as described in operation 256. In this example, the ideal value for contact length $L_c$ may be determined by entering the known values into the sprint velocity equation. As another example, motion variables are monitored that are associated with movements determined to be either efficient or inefficient (for example, during running or sprinting). As one example, overstriding is considered an energy inefficient way to run, resulting in increased ground reaction forces, braking forces and joint loading. Overstriding is a pattern of running where the initial contact of the foot on the ground is far in front of a person's center of mass and typically includes heel striking (i.e. having the heel make initial contact with the ground). To monitor overstriding, one or more sensors may detect the angle of force (or foot inclination angle) relative to a person's center of mass at initial contact with the ground. For example, overstriding may be determined based on the deceleration angle. As one example, the angle of the force vector created by ground contact can be detected with an accelerometer. A positive angle may indicate overstriding, while a near-zero, zero, or negative angle is considered better form (e.g., no to little overstriding). As another example, ground contact isolated to the balls of a sprinter's feet is considered an efficient sprinting technique. To monitor the location of the foot contacting the ground, the system may assess the location and/or angle of acceleration and deceleration forces and ground contact time to determine whether ground contact is by heel strike, fore foot, middle of the foot, or the like. For example, the anterior portion of the foot decelerating faster than the posterior portion may indicate fore foot contact, while the posterior portion decelerating faster than the forefront portion may indicate heel contact.

After operation 258, optionally, the method proceeds to operation 260 and the system determines whether there is a change in activity based on the detected motion characteristics. For example, the system may compare the recently detected motion characteristics to previously detected motion characteristics and determine there is a sufficient change in values indicating a change in activity. For example, a change in value over a particular amount may indicate a change in activity. As one example, a value change of 50% may indicate a change in activity. As another example, the system may determine recently detected motion characteristics fall outside typical range values for the user category determined at operation 252. For example, as discussed above with respect to operation 252, certain ranges of values may be indicative of different activities (e.g., walking, jogging, running, sprinting, aerobics, plyometrics, etc.). As one example, a drastic decrease (e.g., greater than 50% decrease or greater than some other threshold value) in stride frequency or vertical ground force may indicate a change in activity from running to jogging or walking.

If the system determines that there is a change in activity, then the method 250 proceeds to operation 262 and a performance summary is generated. A performance summary may provide overall feedback to a user regarding the specific activity performance. For example, the summary may be a summary of the detected data. The summary may compare the detected data to the ideal values. For example, a performance summary may indicate the user is an overstrider. The summary may provide recommendations for improvement. For example, if the user is consistently making heel strikes with each stride, the summary may instruct the user to attempt to land with the forefoot contacting the ground first. The summary may be stored by the system as historical motion data for the user.

If the system does not detect a change in activity, the method 250 proceeds to operation 264 and the detected motion characteristics are compared to the ideal values stored by the system. As discussed, an ideal value may be a set value, a minimum or maximum threshold value, or a range. The system may determine whether the detected motion characteristic deviates from the set value a particular amount, is above the minimum value, below the maximum value, within the ideal value range, or a particular amount outside of an ideal range. A detected motion characteristic may not be ideal when it deviates a certain degree or percent from an ideal value (e.g., greater than 0.05%, 1%, 5%, 10%, 20% deviation, or the like), exceeds an ideal threshold value (e.g., falls below the minimum or above the maximum), or falls outside an ideal value range. For example, a detected motion characteristic may not be ideal if it is indicative of poor performance (e.g., results in inefficient energy use, increased fatigue, body wear, etc.), inconsistent performance (e.g., deviates from historical user performance), or does not otherwise meet a target or goal (e.g., a target incremental change), or the like. As one example, an ideal force vector angle (e.g., angle of ground impact relative to the ground, e.g., created by contact force with ground) may have a maximum threshold value of 0°, indicative of no overstride. In this example, a detected force vector angle of 10°, when compared to the ideal value, exceeds the threshold (10°>0°), indicating overstriding (e.g., is not ideal). As another example, a detected footstrike location may be 2 cm posterior to the ball of the foot, which when compared to the ideal value (e.g., the ball of the foot) deviates 2 cm from the ideal location (or if the person has a foot size of 24 cm, for example, the deviation is about 8%) (e.g., is not ideal). In another example, for a runner with a height of 170 cm striving for a pace of 7 min./mile, an ideal stride length based on a certain cadence is 130 cm. A detected stride length of 110 cm, when compared to the ideal stride length, is about 15% shorter than the ideal stride length (e.g., leading to a slower pace such that the detected stride length is not ideal). As yet another example, an ideal vertical ground force may be 2.5 times the person's body weight, such that a detected vertical ground force of 5 times the person's body weight doubles the ideal value (e.g., is not ideal). As another example, an ideal value may be a 5% increase in force each run. If a user only increases the force 1% from the prior run, then the detected value deviates 4% from the ideal value (e.g., is not ideal).

After operation 264, the method 250 proceeds to operation 268 and motion feedback (e.g., biofeedback) is transmitted to a user based on the comparison. Motion feedback is feedback related to the user's movement. For example, motion feedback may include feedback related to the factors monitored by the system related to movement performance, such as, for example, ground contact time, ground contact balance, stride length, stride width, stride frequency, stride type, vertical force applied to ground, horizontal force, rate of force development, mass specific force, angle of force, momentum, resistance, acceleration/deceleration, center of mass/gravity, support displacement, pace, biometric data (e.g., recovery rate, heart rate variability, etc.), and the like.

As discussed above, feedback may be transmitted to a user via feedback devices 104. Feedback may be positive or negative. For example, positive feedback may indicate the user's detected movements are ideal, within an acceptable deviation from an ideal value, do not exceed an ideal value threshold, within an ideal value range, or the like. For example, positive feedback may indicate ground contact time, stride frequency, stride length, vertical ground force, support displacement, footstrike location, and the like, are ideal or near ideal. As another example, positive feedback may indicate the user achieved the ideal incremental change (e.g., increased ground contact force 5% over the previous run, where 5% increase is the ideal value). Positive feedback may indicate to a user that the user is performing properly or adequately (e.g., efficiently using energy, reducing fatigue and body wear, has proper posture, and the like) or consistently (e.g., producing similar or the same results over time), or improving, or the like. As another example, negative feedback may indicate the user's detected movements are not ideal, greatly deviate from an ideal value (e.g., exceed an acceptable deviation range), exceed an ideal value threshold, fall outside an ideal value range, or the like. Negative feedback may indicate to a user that the user's performance is inadequate (e.g., inefficiently using energy, increasing fatigue and body wear, has improper posture, and the like), inconsistent (e.g., varying results over time), failing to track target improvement goals, or the like.

Feedback may be presented to a user as visual, audible, and/or haptic information. Visual feedback may include different colors, icons, text or the like appearing on a wearable device (e.g., a smart watch, glasses, goggles, etc.). Audible feedback may include an alert, beep, change in song frequency or pitch, or the like. Haptic feedback may include different intensities, timing, or locations of vibrations or electrical impulses. The feedback presentation may vary depending on whether the feedback is positive or negative. For example, positive feedback may be indicated by an audible frequency (e.g., high or low), visual indicator (e.g., color, graphic, text, etc.), or haptic indicator (e.g., vibration intensity, frequency, location) that varies from the audible frequency, visual indicator, or haptic indicator indicating negative feedback. For example, as discussed, positive feedback may be indicated by a "better" or more pleasant tone (e.g., softer, quieter, less frequent, steady, etc.), while negative feedback may be indicated by a "worse" or less pleasant tone (e.g., harsher, louder, more frequent, etc.). In this example, the tone may become worse as the detected value deviates further from the target value or range or the tone may become better as the detected value gets closer to the target value or range. By providing feedback that is more or less pleasurable or pleasant to the user depending on the deviation from a target range, the user can internalize the feedback more quickly and correct his or her motion characteristics corresponding. In another example, positive feedback may be indicated by a green flash, while negative feedback is indicated by a red flash. As another example, positive feedback may be indicated by a vibration on the top of a user's wrist, while negative feedback is indicated as a vibration on the bottom of the user's wrist. As another example, positive feedback may be one feedback type (e.g., audible, haptic, visual) and negative feedback may be another feedback type.

The feedback presentation may also vary based on the level of variance/deviation from the ideal value or range, or, in other words, be directly correlated to the suggested improvement or change needed by the user's actions in order to reach or approach the ideal values. As one example, the volume intensity or pitch may increase the greater a user's movement deviates from an ideal value. As another example, a color or light may get brighter or darker the more a user's movement deviates from an ideal value. The change in the presentation (e.g., greater volume or brighter color) may vary in proportion to the deviation from the ideal value. For example, audible feedback may be loudest when the user deviates from the ideal value a maximum amount (e.g., the user needs to adjust applied ground force by a maximum amount) and decreases proportionally as the deviation is reduced. In this manner, a user may detect and adapt his or her motions in accordance with the feedback and understand whether the last action was an improvement over past actions. As one example, a loud beep may indicate to a user that the user is overstriding by 40%. The user may then aim to adjust his or her stride with the next stride to account for the overstriding. Upon system detection of the next stride, a quieter beep, about half the volume of the first beep, may indicate to a user that the user is overstriding by 20%. The user may again adjust his or her stride. In this example, silence may indicate the user's stride is ideal (e.g., no overstriding). In this manner, the user may keep adjusting his or her stride until the feedback indicates the user's stride is ideal (e.g., until no beep is sounded).

The feedback type and/or presentation may also vary for different motion characteristics. For example, vertical force may be indicated by one feedback type (e.g., visual feedback) while ground contact time may be represented by another feedback type (e.g., audio feedback). As another example, stride length may be represented by one type of visual presentation (e.g., a color gradient) while stride frequency may be represented by another type of visual presentation (e.g., a graphic). In this manner, a user may adjust his or her motion for different characteristics.

Feedback may include a recommendation for motion adjustments. For example, the system may determine adjustments based on the comparison of the detected motion characteristics to the ideal values. For example, where a detected motion characteristic deviates from an ideal value by a certain amount, the system may recommend the user alter the motion by the deviation amount to reach the ideal value. For example, where the user contacted the ground at 10% more force than the ideal force value, the system may recommend the user reduce the contact force by 10%, e.g., a visual display or graphic may indicate the amount of force reduction necessary to reach the ideal value (e.g., a smart watch may display text, such as "reduce force 10%").

The timing of feedback transmission may vary. For example, feedback may be delivered in real-time. As discussed, the feedback may be delivered to the user substantially simultaneously or as close to the actual movement generating the feedback values such that the user can correct or vary his or her motion in real time and be provided dynamically variable feedback adjusting to the user's changes. For example, feedback may occur as quickly as or quicker than the series of movements. As one example, feedback may be transmitted to a user in between strides (e.g., while a user is mid-stride before the next foot contacts the ground). In this case, the user may receive feedback regarding the prior stride or contact with the ground before the next stride or contact is made. In this manner, a user may correct or vary his or her motion in real time until the user receives positive feedback.

As another example, feedback may occur after a certain number of movements, after a certain amount of time, after an activity stage, or the like. As one example, for a sprinter, feedback may be provided after the first 2-4 steps, or after the starting stage. Feedback may be real-time as it is collected or feedback may be cumulative. In the example of sprinter feedback delivery after the first 2-4 steps, feedback may be provided on force vector data for each step and/or cumulative feedback may be provided on the total distance covered and the time to cover that distance once the 4 steps are completed. As another example, feedback may be provided during a particular activity stage or after leaving the activity stage. For example, the system may determine when a sprinter is in a maximum velocity stage (e.g., based on historical data) and provide feedback during that stage. As another example, the system may determine the maximum velocity stage has ended and provide feedback on motion data collected during that phase (e.g., top speed, distance covered, number of strides, etc.).

In some instances, detected movements may occur more rapidly than the system can provide feedback. For example, new motion characteristics may be detected before feedback related to previously detected motion characteristics is transmitted to the user. In these instances, more recently detected motion characteristics may override previously detected motion characteristics and feedback related to the most recently detected motion characteristics may be transmitted to the user. In this manner, a user can alter/correct the most recent movement.

After operation 268, the method 250 proceeds to operation 258 and motion characteristics are again detected, as discussed above. In this manner, the system may continuously detect a user's motion during an activity and provide real time feedback until the activity ends or changes to a new activity.

Figure 5:
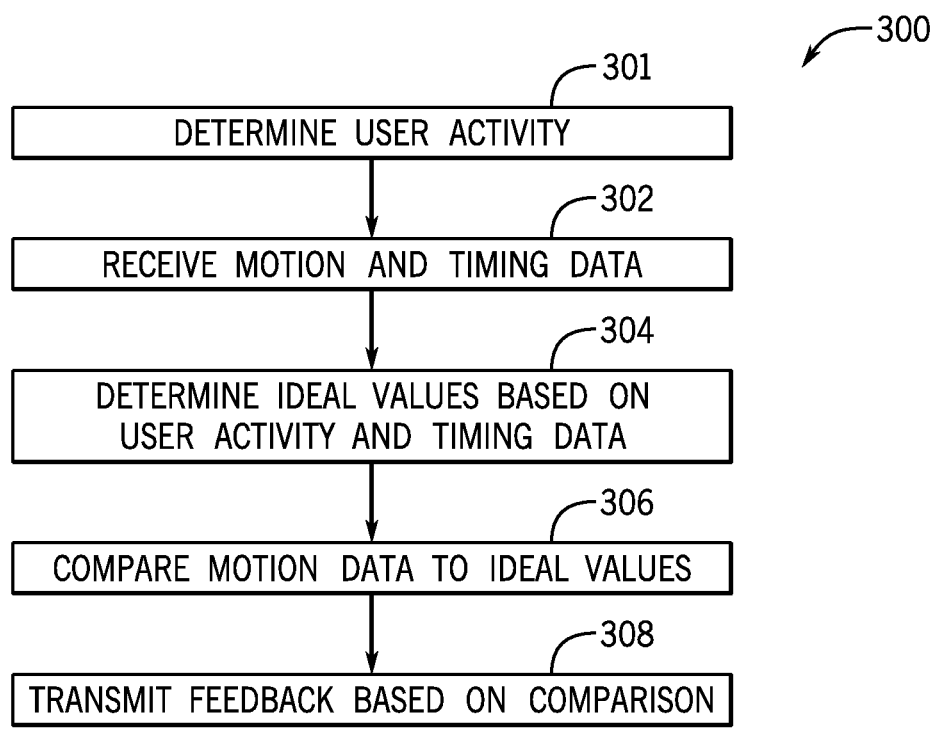
FIG. 5 is a flow chart illustrating a method for using the system of FIG. 1 to track stage-specific user movement and provide motion feedback during an activity.

FIG. 5 illustrates a method for using the system 100 to track stage-specific user movement and provide motion feedback during an activity. The method 300 begins with operation 301 and user activity is determined. User activity is determined in a similar manner as the user category discussed above with respect to operation 252 of method 250. For example, user activity may be input by a user or determined by the system based on a trial run. User activity may include aerobics, plyometrics, walking, jogging, running, sprinting, sports, or other exercise. The user activity may have different activity stages. For example, sprinting may have a starting stage, an acceleration stage, a maximum velocity stage, and a deceleration stage. The level of activity and motion characteristics may vary based on the activity stage.

After operation 301, the method 300 proceeds to operation 302 and motion and timing data is received. Motion data may be detected in a similar manner as discussed above with respect to operation 258 of method 250. For example, motion data may be collected by one or more detection devices 112, 114. Motion data may include data related to speed, movement efficiency, posture, and other indicators of performance. For example, as discussed above, motion data may include stride (e.g., length, width, frequency, type), ground interaction (e.g., ground contact time, vertical force applied, mass specific force, angle of force), foot strike location, acceleration/deceleration, body positioning, support displacement, pace, and the like. The detection devices 112, 114, or another system component in communication therewith, may include a timing component (e.g., a timer) that provides a timestamp for the motion data as it is collected. For example, the timing information may be included as metadata with the motion data. The timing data may indicate the amount of time lapsed from the start of the activity.

After operation 302, the method 300 proceeds to operation 304 and ideal values are determined based on the user activity and timing data. The system 100 may have stored ideal values associated with the user activity. For example, as discussed above, running and sprinting, two different activities, may have different ideal values associated with proper posture, efficient energy use, reduced fatigue, reduced bodily injury, and the like. An activity may also have different ideal values at different stages of the activity. For example, sprinting may have different ideal values during the acceleration stage versus the constant speed stage. As one example, ideal vertical force exerted may vary at the acceleration stage versus the constant speed stage. Based on the determined user activity and the received timing data, the system may determine applicable ideal values. For example, in the sprinting example, the determined user activity at operation 301 is sprinting, and timing data indicating the motion data was collected in the first 4 seconds would indicate the motion data was collected during the acceleration stage. In this case, the system would associate the motion data received at operation 302 with ideal values for a sprinting acceleration stage. The ideal values for each activity stage may be stored by the system or accessible through a third party database.

After operation 304, the method 300 proceeds to operation 306 and the motion data is compared the ideal values. The motion data may be compared to the ideal values in a similar manner as discussed above with respect to operation 260 of method 250. For example, as discussed, the system may determine whether the detected motion data deviates from an ideal value a particular amount, is above an ideal minimum value threshold, below an ideal maximum value threshold, or within an ideal value range. The motion data is not ideal when it deviates a certain degree or percent from an ideal value, exceeds an ideal threshold value (e.g., falls below the minimum or above the maximum), or falls outside an ideal value range.

After operation 306, the method 300 proceeds to operation 308 and feedback is transmitted to the user based on the comparison. For example, feedback data is generated and transmitted to a user in a similar manner as discussed above with respect to operation 262 of method 250. As discussed above, feedback may be transmitted to a user via feedback devices 104. Feedback may be positive (e.g., indicating movement is ideal or near ideal) or negative (e.g., indicating movement is not ideal and likely needs to be adjusted). Feedback may be presented to a user as visual, audible, and/or haptic information. The feedback presentation may vary depending on whether the feedback is positive or negative. Where the ideal values vary based on the activity stage, positive feedback for a particular movement at one stage may become negative feedback at another stage if the user fails to adjust the user's motion based on the ideal values at the particular activity stage. For example, during the acceleration stage, the ideal force vector angle relative to the ground may be less than during the constant speed stage, such that the user must increase the force vector angle relative to the ground as the user transitions from the acceleration stage to the constant speed stage. If the user does not increase the force vector angle, the user may receive positive feedback during the acceleration stage and negative feedback during the constant speed stage, the negative feedback indicating the user needs to increase the force vector angle.

The technology described herein may be implemented as logical operations and/or modules in one or more systems. The logical operations may be implemented as a sequence of processor-implemented steps executing in one or more computer systems and as interconnected machine or circuit modules within one or more computer systems. Likewise, the descriptions of various component modules may be provided in terms of operations executed or effected by the modules. The logical operations may be implemented by a single system component (e.g., a detection device, feedback device, or user device) or by multiple system components. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method for providing motion biofeedback to a user, comprising:
   determining, by a processor, an activity type of an activity performed by the user;
   determining, by the processor, a target value for one or more motion characteristics associated with the activity, wherein the target value is determined by historical collected motion data;
   receiving, from a detection device including one or more of an accelerometer, a gyroscope, a magnetometer, a compass, a pressure sensor, a force sensor, location sensor, or a global positioning sensor, motion data related to the activity as the user performs the activity, the motion data comprises a first deceleration force detected during ground contact of a first foot on a surface occurring from a first stride;
   comparing, by the processor, the motion data to the target value; and
   transmitting the motion biofeedback to a feedback device based on the comparison to the target value, wherein:
   the motion biofeedback corresponds to a motion adjustment proportional to a deviation of the motion data relative to the target value; and
   the motion biofeedback is transmitted to the feedback device before a second deceleration force is detected during a second ground contact of one of the first foot or a second foot on the surface occurring from a second stride.

2. The method of claim 1, wherein the target value is a percentage increase or decrease of the historical collected motion data.

3. The method of claim 1, wherein the motion data is related to a foot deceleration location and the method further comprises determining, by the processor, a footstrike location based on the foot deceleration location, wherein the motion biofeedback corresponds to a footstrike location adjustment when the footstrike location deviates from an ideal footstrike location.

4. The method of claim 1, wherein the first deceleration force comprises a ground contact force, and the target value is an increase in the ground contact force from historical collected ground contact force data.

5. The method of claim 1, wherein the motion data is ground contact time, and the target value is a percentage decrease in the ground contact time from historical collected ground contact time data.

6. The method of claim 1, wherein the first deceleration force comprises a force vector angle at the ground contact, and the target value is a percentage decrease in force vector angle from historical collected force vector angle data until the force vector angle reaches zero degrees.

7. The method of claim 1, wherein the historical collected motion data is the last stored collected motion data related to the one or more motion characteristics.

8. The method of claim 1, wherein the activity is one of sprinting, walking, or long distance running, and the one or more motion characteristics comprise ground contact force, force vector angle of the ground contact, and ground contact time.

9. The method of claim 1, wherein determining the activity comprises:
   comparing, by the processor, the motion data to activity data stored in memory associated with the processor;
   determining, by the processor, motion data values correlate to one or more motion characteristic values associated with a stored activity based on the comparison of the motion data and the stored activity data; and
   determining the activity performed by the user is the stored activity.

10. The method of claim 1, further comprising determining, by the processor, a current activity stage of the activity based on the activity type and the motion data, wherein the target value and the motion biofeedback is based on the current activity stage.

11. A method for providing stage-specific motion feedback to a user, comprising:
   determining, by a processor, an activity type of an activity performed by the user;
   receiving, from a detection device including one or more of an accelerometer, a gyroscope, a magnetometer, a compass, a pressure sensor, a force sensor, location sensor, or a global positioning sensor, motion data comprising a first motion characteristic value corresponding to a motion characteristic associated with the activity type;
   determining, by the processor, a current activity stage of the activity based on the activity type and the motion data;
   determining, by the processor, an ideal value for the motion characteristic based on the current activity stage;
   comparing, by the processor, the first motion characteristic value to the ideal value to determine a motion adjustment to achieve the ideal value; and
   generating, by the processor, the stage-specific motion feedback related to the motion adjustment, wherein the stage-specific motion feedback is dependent on the current activity stage; and
   providing, by the processor, the stage-specific motion feedback during the current activity stage before detecting a second motion characteristic value.

* * * * *